US008578757B2

(12) United States Patent
Ren et al.

(10) Patent No.: US 8,578,757 B2
(45) Date of Patent: Nov. 12, 2013

(54) SYSTEM FOR HYDROGEN SENSING

(75) Inventors: Fan Ren, Gainesville, FL (US); Jenshan Lin, Gainesville, FL (US); David Paul Norton, Gainesville, FL (US); Stephen John Pearton, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 902 days.

(21) Appl. No.: 12/443,297

(22) PCT Filed: Oct. 5, 2006

(86) PCT No.: PCT/US2006/038758
§ 371 (c)(1),
(2), (4) Date: Mar. 3, 2010

(87) PCT Pub. No.: WO2008/041983
PCT Pub. Date: Apr. 10, 2008

(65) Prior Publication Data
US 2010/0170325 A1 Jul. 8, 2010

(51) Int. Cl.
*G01N 7/04* (2006.01)
*G01N 27/00* (2006.01)

(52) U.S. Cl.
USPC .......................... 73/31.05; 73/31.06; 257/253

(58) Field of Classification Search
USPC ................................ 73/31.05, 31.06; 257/253
See application file for complete search history.

(56) References Cited

U.S. PATENT DOCUMENTS

2006/0122504 A1* 6/2006 Gabara et al. ................. 600/437
2009/0141767 A1* 6/2009 Cummins ..................... 374/142

OTHER PUBLICATIONS

L. C. Tien, P. W. Sadik, D. P. Norton, L. F. Voss, S. J. Pearton, H. T. Wang, B. S. Kang, F. Ren, J. Jun, and J. Lin, "Hydrogen sensing at room temperature with Pt-coated ZnO thin films and nanorods," App. Phys. Lett. 87, 222106, published online Nov. 21, 2005.*
Jerry Chun-Pai Jun, "Design and testing of a self-powered wireless hydrogen sensing platform," Thesis (M.S.) University of Florida, May 2006.*
R. Amirtharajah, A. Chen, D. Thaker, F. T. Chong, "Circuit interfaces and optimization for resistive nanosensors," Nanosensing: Materials and Devices II, Proc. of SPIE vol. 6008, 60080J (2005).*
H. T. Wang, B. S. Kang, F. Ren, L. C. Tien, P.W. Sadik, D. P. Norton, S. J. Pearton, J. Lin, "Hydrogen-selective sensing at room temperature with ZnO nanorods," Appl. Phys. Lett. 86, 243503, (2005).*

(Continued)

*Primary Examiner* — Lisa Caputo
*Assistant Examiner* — Punam Roy
(74) *Attorney, Agent, or Firm* — Saliwanchik, Lloyd & Eisenschenk, P.A.

(57) ABSTRACT

Exemplary embodiments provide a self-powered wireless gas sensor system and a method for gas sensing using the system. The system can be used to detect and constantly track a presence of various gases including hydrogen, ozone and/or any hydrocarbon gas, and remotely transmit the sensing signal. The system can include a low power gas sensor that consumes less than about 30 nano-watts of power. As a result, the system can detect the presence of hydrogen at about 10 ppm. The sensor can also provide a fast response time of about 1-2 seconds. In various embodiments, the system can be physically small and packaged with all components assembled as a single compact unit.

25 Claims, 4 Drawing Sheets

(56) References Cited

OTHER PUBLICATIONS

J. D. Adams, G. Parrott, C. Bauer, T. Sant, L. Manning, et al., "Nanowatt chemical vapor detection with a self-sensing, piezoelectric microcantilever array," Appl. Phys. Lett. 83, 3428 (2003).*

Lin, et al., "Robust Self-Powered Wireless Hydrogen Sensor", Florida Universities Hydrogen Review 2005; Florida Solar Energy Center; Nov. 1-4, 2005. (retrieved from http://www.hydrogenresearch.org/NRM_Nov05/UF-Lin-WIreless%20Hydrogen%20Sensor-Nov05.pdf).

Ren, et al., "Nanorod and Nanotube Based Gas Sensors", Florida Universities Hydrogen Review 2005; Florida Solar Energy Center; Nov. 1-4, 2005. (retrieved from http://www.hydrogenresearch.org/NRM_Nov05/UF-Ren-Nanorod-Nov05.pdf).

International Application No. PCT/US06/38758, Written Opinion of the International Searching Authority and International Search Report, completed Jul. 18, 2008.

* cited by examiner

SYSTEM FOR HYDROGEN SENSING

GOVERNMENT RIGHTS

This invention was made with government support under Contract No. NAG3-2930 awarded by the National Aeronautics and Space Administration. The government has rights in the invention.

FIELD OF THE INVENTION

This invention relates generally to gas sensing systems, and, more particularly, to a wireless, low power gas sensing system.

BACKGROUND OF THE INVENTIONS

Recently, hydrogen has attracted attention as an energy source for a wide variety of industrial and scientific uses, in particular, as a clean fuel substitute for fossil fuel. Because hydrogen is an extremely flammable and explosive gas, hydrogen sensors must be employed to monitor the environment where hydrogen is utilized. This can not only safeguard the apparatus and associated operating personnel, but can also ensure the efficiency and operational integrity of the hydrogen powered apparatus. Hydrogen sensors, for example, for use with coal-derived gas and hydrogen fuel cells, require low power consumption and a short response time in the range of 1-2 seconds Conventional hydrogen sensors, however, use high operating bias voltage which requires high power levels. Another drawback of conventional hydrogen sensors is that they monitor the conductivity change of the sensing element upon exposure to the hydrogen. This results in detection times typically in the range of minutes at room-temperature. A conventional solution for decreasing the response time is to heat up the sensing element. However, this adds weight and dramatically increases the power requirements of the sensor. In addition, conventional hydrogen sensors trigger a detection signal simply by sounding-off an alarm. In some cases, it may be desirable to send indication of detection to a remote location and/or to locations out of hearing range of the alarm.

Thus, there is a need to overcome these and other problems of the prior art and to provide a system for hydrogen sensing with low power consumption, fast response, and signal transmission to a remote location. It is further desirable to provide a system that can operate by harvesting energy.

SUMMARY OF THE INVENTION

According to various embodiments, the present teachings include a system for gas sensing. In the system, a gas sensor with a low power consumption of less than 30 nano-watts is configured to provide a response to a gas. The response to the gas can be an electrical signal amplified by a differential detection interface (DDI) connected to the low power gas sensor. A microcontroller is connected and programmed to process the electrical signal, which is then wirelessly transmitted by a transmitter.

According to various embodiments, the present teachings also include a method for gas sensing. In the method, an analyte gas is detected with a sensing component disposed in a gas sensor with a low power consumption of less than about 30 nano-watts. An electrical signal is outputted by a differential detection interface (DDI) in response of the detected analyte gas. The electrical signal is then processed and wirelessly transmitted by a microcontroller and a transmitter.

According to various embodiments, the present teachings further include a system for remote hydrogen sensing. The system includes a sensor device including a low power hydrogen sensor providing sensor data in response to hydrogen, a differential detection interface connected the hydrogen sensor with the microcontroller to amplify and process the sensor data, and a wireless transmitter connected to the microcontroller to transmit the processed sensor data. The system also includes a central monitoring station including a wireless receiver configured to receive the sensor data signal from the wireless transmitter of the sensor device. The system further includes a power source to power the sensor device. The power source includes at least one of vibrational energy harvesters, solar energy harvesters and the battery.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Exemplary embodiments provide a low power, wireless gas sensor system. In particular, the system can be used to detect and constantly track a presence of various gases, and remotely transmit the sensing signal. The system can be powered through a power source including vibrational energy harvesters, solar energy harvesters and/or batteries. As a result, the system can detect hydrogen at about 10 ppm, utilize less than 30 nano-watts to power the gas sensor, and provide a response time of about 1 to about 2 seconds. In addition, the system can be physically small and packaged with all components assembled as a single, lightweight, compact unit.

Reference will now be made in detail to exemplary embodiments of the invention, an example of which is illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

Figure 1:
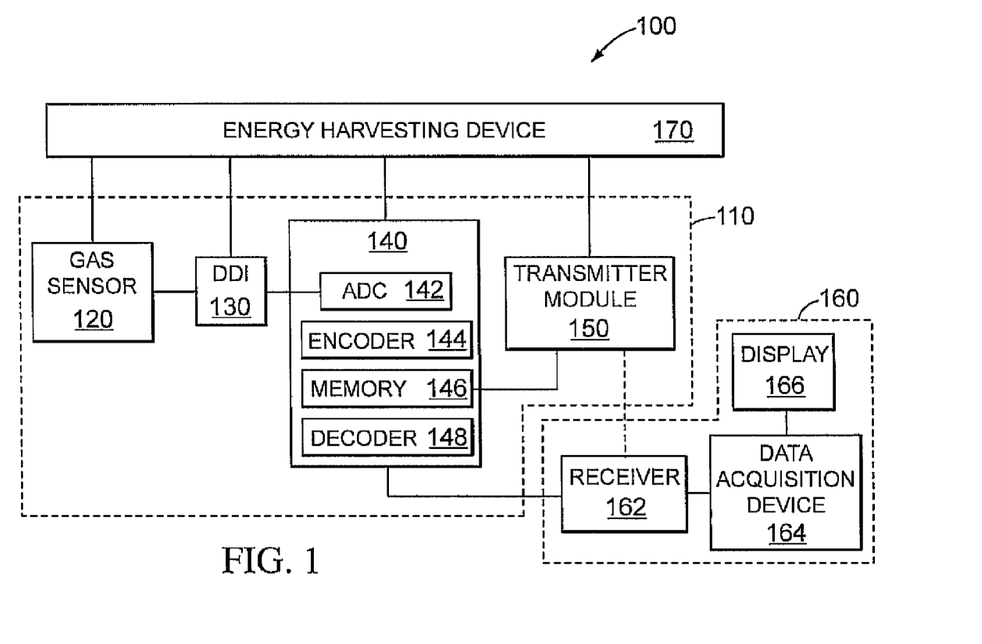
FIG. 1 depicts an exemplary system for a self-powered wireless gas sensor in accordance with the present teachings.

FIG. 1 depicts an exemplary wireless gas sensor system 100. As shown, the system 100 can include a sensor device 110, a central monitoring station 160, and a power source 170. Although the power source 170 is depicted as an energy harvesting device in FIG. 1, one of ordinary skill in the art will understand that power source 170 can be a battery or another power source. The sensor device 110 can wirelessly transmit a detected signal to the central monitoring station 160. The power source 170 can connect to and power one or more component of the sensor device 110. In various embodiments, the system 100 can be assembled in a single compact module.

In various embodiments, the system 100 can be used for any environment that needs gas detection and/or constant gas monitoring/tracking. Detectable gases can include, but are not limited to, hydrogen, ozone, or any hydrocarbon gas, such as, for example, ethylene.

As shown in FIG. 1, the sensor device 110 can include a gas sensor 120, a differential detection interface (DDI) 130, a microcontroller 140, and a transmitter module 150. The sensor device 110 can be exposed to detect an analyte gas, for example, hydrogen with a concentration of, for example, 5, 10, 200, or less than 500 ppm.

The gas sensor 120 can be a low power gas sensor and include various sensor components to selectively respond to the analyte gas with a low power consumption. The sensor components can be formed of, but are not limited to, one or more of ZnO nanorods, ZnO or GaN Schottky diodes, AlGaN/GaN HEMT (high electron mobility transistors) and/or MOS (metal-oxide semiconductor) transistors.

In various embodiments, metal catalysts, for example, Pt, Pd, Ni, Au, Ag, Ti, or their alloys can be coated on or doped in those sensor components. The metal catalysts can provide good catalytic activity at room temperature and can dissociate the hydrogen molecule adsorbed to the surface into hydrogen atoms. A portion of the hydrogen atoms can then diffuse through the metal catalysts and be adsorbed to the interface between the metal and the sensing components (e.g., ZnO or GaN). Accordingly, the metal coatings or dopings can improve the sensing selectivity of gas and provide a response time of 2 seconds or less. In various embodiments, the response time for the system 100 to sense hydrogen or other gases can be at a variety of ranges. For example, the GaN based sensing components in HEMT (high-electron mobility transistor) or Schottky diode can provide a sensing response time in a range of such as about 1-2 seconds, while the ZnO nanorods based sensing components can provide a sensing response time in a range of such as about 1-3 minutes.

ZnO nanorods can be used as a sensing component in the gas sensor 120. As used herein, the term "ZnO nanorod" refers to any cylindrical shaped ZnO structure with a diameter of about 100 nanometers or less. The ZnO nanorods can include, for example, single ZnO nanorods and multiple ZnO nanorods.

In addition, the term "nanorods" also refers to nanowires, nanotubes, such as, for example, single wall nanotubes, multiwall nanotubes, and their various functionalized and derivatized fibril forms, which include nanofibers. The nanofibers can be fibrils with diameters of 100 nm or less in at least one form of thread, yarn, fabrics, etc.

Generally, the metal oxide ZnO can be an attractive material for specific sensing application because of its wide bandgap of 3.2 eV, the ease of synthesizing nanostructures, the availability of heterostructures and the bio-safe characteristics. Accordingly, ZnO can be a material currently used in the detection of gas, for example, hydrogen, pH, humidity, UV light and chemicals. For example, when ZnO is exposed to hydrogen and/or temperature change, the resistance (or conductivity) of the material ZnO can be changed, showing a presence or a change of the hydrogen and/or the temperature.

The ZnO nanorods can have a length of, for example, about 2 nm to about 10 μm and a diameter of about 30-150 nm. The ZnO nanorods can be synthesized by various methods known to one of ordinary skill in the art, such as, for example, site-selective molecular beam epitaxy disclosed as in "Hydrogen-Selective Sensing at room Temperature with ZnO Nanorods", *Applied Physics Letters*, Vol. 86, page 243-503, 2005, and "Hydrogen and Ozone Gas Sensing using Multiple ZnO Nanorods", *Applied Physics A*, Vol. 80, page 1029-1032, 2005.

The ZnO nanorods can be placed in an array for the low power gas sensor 120. The ZnO nanorods in an array can create a large chemically sensitive surface-to-volume ratio which is needed for high sensitivity in hydrogen sensing. Moreover, ZnO nanorods can also be produced cost-wisely, and highly compatible with other microelectronic devices. For example, multiple ZnO nanorods can be grown on very cheap substrates such as glass and can be simply processed into sensors, such as the gas sensor 120.

Catalytic coatings or dopings (e.g., Pt, Pd or Ni) can be used to further increase the ZnO nanorods hydrogen sensing mechanisms and to enhance the device's sensitivity to hydrogen. Low power gas sensor 120, for example single ZnO nanorods coated with Pt/Pd clusters, can provide the benefit of operating at nano-watt power levels, for example, less than about 30 nano-watts. In various embodiments, the gas sensor can operate at about 10 to about 30 nano-watts. Multiple ZnO nanorods can also be coated with Pt/Pd cluster providing increased hydrogen sensing selectivity and a low power consumption of about 0.2-0.6 μW. Moreover, if desired, the Pt/Pd cluster can be coated on multiple ZnO nanorods by only one level of metal deposition using a simple shadow mask.

Figure 2:
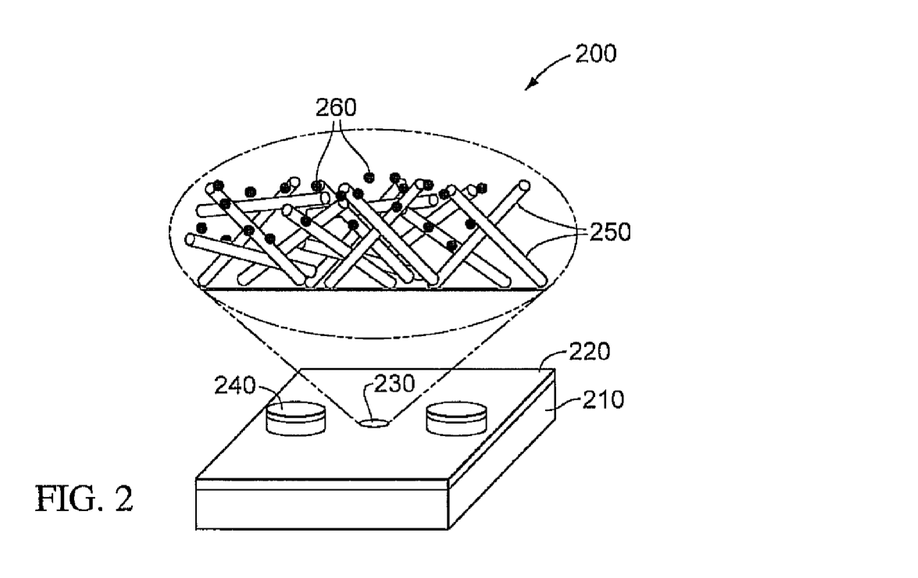
FIG. 2 depicts an exemplary gas sensor using multiple ZnO nanorods as sensing components in accordance with the present teachings.

FIG. 2 depicts an exemplary gas sensor 200 using multiple ZnO nanorods as sensing components. The gas sensor 200 can include a substrate 210, an active layer 220, sensing components 230 and contacts 240.

As shown, the active layer 220 can be formed on the substrate 210, which can be, for example, an alumina $Al_2O_3$ substrate. The active layer 220 can include sensing components 230, which can be, for example, multiple ZnO nanorods 250 coated with metal catalyst Pt 260. The sensing components 230 can be configured between the contacts 240. The contacts 240 can be, for example, sputtered Al/Ti/Au electrodes with a separation of, for example, less than 30 μm.

In the gas sensor 200, the measured electrical signal, for example, the measured currents can be only due to the transport through the sensing components 230 themselves (i.e., the Pt 260 coated multiple ZnO nanorods 250). For example, the current-voltage characteristics of the Pt 260 coated multiple ZnO nanorods 250 can be linear with exemplary currents of such as 0.8 mA at an applied bias of such as 0.5 V.

Figure 3:
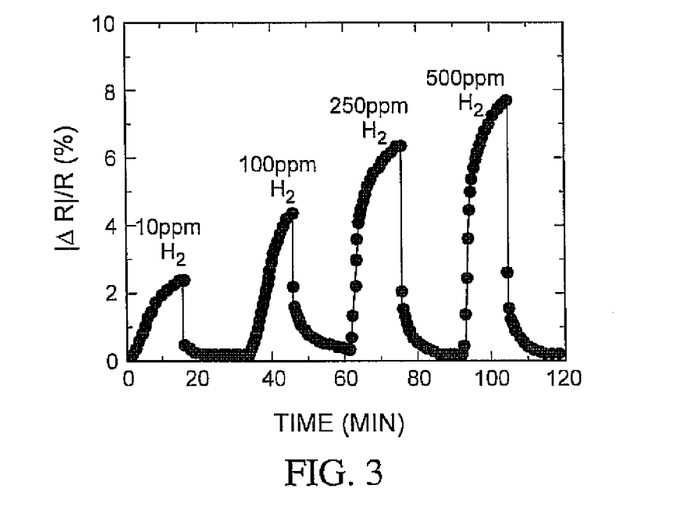
FIG. 3 depicts an exemplary result from the gas sensor shown in FIG. 2 with a relative (or transient) response to various levels of hydrogen concentrations in accordance with the present teachings.

FIG. 3 depicts an exemplary result from the gas sensor 200 with a relative (or transient) response to various levels of hydrogen concentrations. As shown, the Pt coated ZnO nanorods can detect hydrogen of about less than 10 ppm with relative responses (i.e., $\Delta R/R$ in FIG. 3, where R is a resistance of the sensing components and $\Delta R$ is a resistance change of the sensing components) of more than 2.6% at 10 ppm and more than 4.2% at 500 ppm for a 10-minute hydrogen-exposure. As also can be shown, the relative transient response can be a function of hydrogen concentration, that is, the transient response can increase as the hydrogen concentration increases.

In some embodiments, metal catalysts coated ZnO can be fabricated in a Schottky diode for the gas sensor 120. In other embodiments, III-V compound semiconductor materials can be used to form the sensing components. Examples of the group III element can include Ga, In or Al, while examples of the group V element can include As, Sb, N, or P. Thus, III-V semiconductor alloy compositions can be described by the combination of III-V elements, such as, for example, InGaAs, AlGaAs, AlGaInAs, GaNAs, InGaAsP, or GaInNAs. Exemplary sensing components from the group III-V can include GaN for Schottky diodes, AlGaN/GaN for high electron mobility transistors (HEMT) and/or metal-oxide semiconductor (MOS) transistors. The III-V sensing components can provide unique properties, for example, the GaN based devices can be used in harsh environments such as with a high temperature of more than 550° C. In other embodiments, II-VI compound semiconductor materials, for example CdS, can be used as the sensing component for the gas sensor 120.

In various embodiments, the gas sensor 120 can further include passivated (i.e., non-active) sensing components as a reference for gas detections, which can eliminate other effects such as a temperature effect on the detection. That is, the reference can provide unchangeable characteristics upon exposure to analyte gases. For example, the passivated ZnO nanorods encased in glass can be used as a reference for ZnO nanorods. In various embodiments, the gas sensor 120 can provide high sensitivity, rapid response to stimuli, reversibility and also be lightweight.

Turning to FIG. 1, the differential detection interface (DDI) 130 can be a sensor interface between the gas sensor 120 and the digital signal processing device in the microcontroller 140. Specifically, the DDI 130 can be used to detect the resistance changes of the sensing components (e.g., the ZnO nanorods) in the gas sensor 120, amplifier the signal, and then output an electrical signal for example a voltage sensing signal to the A/D Converter (ADC) in the microcontroller 140. In addition, the DDI 130 can be a low power and portable sensor interface for gas detections.

Figure 4:
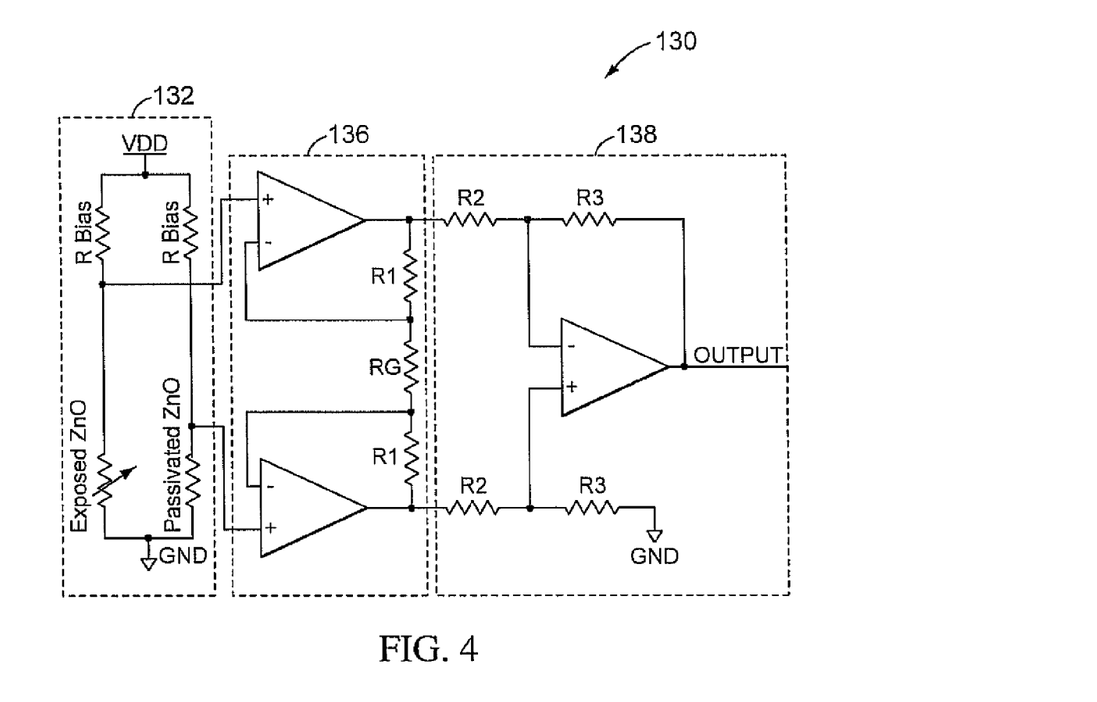
FIG. 4 depicts an exemplary sensor interface circuit for a differential detection interface (DDI) in accordance with the present teachings.

FIG. 4 shows an exemplary sensor interface circuit for the DDI 130. As shown, the DDI 130 can be a combination of a Wheatstone Resistive Bridge 132, a gain amplifier stage 136, and a difference amplifier 138. The Wheatstone Resistive Bridge 132 and the gain amplifier stage 136 can output an amplified electrical signal from the response of hydrogen sensor 120 to the analyte gas. The amplified signal can be outputted from the difference amplifier 138.

The Wheatstone Resistive Bridge 132 can include a standard Wheatstone bridge and a resistive bridge known to those of ordinary skill in the art. As shown, the resistive bridge can be connected to the exposed (i.e., active) and the reference (i.e., passivated or non-active) sensing components in the gas sensor 120, for example, the exposed ZnO nanorods and the passivated ZnO nanorods. With this reference resistor, only the resistance changes caused by the exposure to the gas can be detected, which can exclude those caused from the working environment, such as the ambient temperature. When exposing ZnO nanorods to an analyte gas, the resistance of the exposed ZnO nanorods can vary with respect to how much and how long the device has been exposed to.

Figure 5:
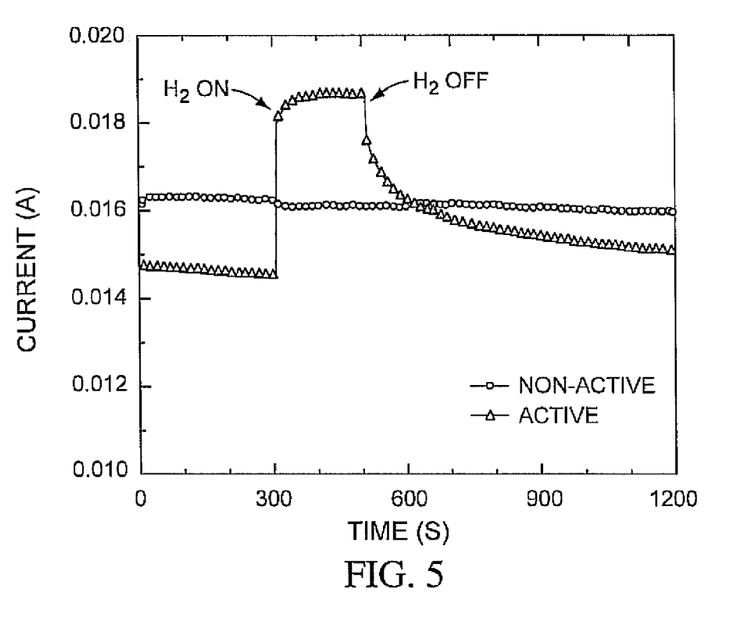
FIG. 5 depicts exemplary sensing results for a gas sensor with an active and a non-active (i.e., passivated) ZnO nanorods upon exposing to hydrogen in accordance with the present teachings.

FIG. 5 depicts exemplary sensing results from a DDI 130 for a gas sensor 120 with an active and a non-active (i.e., passivated) ZnO nanorods upon exposing to hydrogen. The gas sensor 120 can be exposed to air with 1% hydrogen at, for example, room temperature. In various embodiments, the gas sensor 120 can be used in various temperature environments, such as, for example, with a higher temperature of about 50° C. (not shown). During the measurement, the gas sensor 120 can be biased at, for example, about 2.5V. As shown in FIG. 5, the active ZnO nanorods can provide a change in current indicating a response to the hydrogen exposure, while the non-active ZnO nanorods can provide no changes in current.

Referring back to FIG. 4, the gain amplifier stage 136 can be a non-inverting gain amplifier to buffer, amplify, and/or provide a high impedance input to the Wheatstone Bridge of 132, before the signal from the Resistive Bridge of 132 can be processed by the amplifier 138. The gain amplifier stage 136 can also be an instrumentation amplifier. The gain amplifier stage 136 can include Op-Amps, which can be selected by their power requirements and their typical input offset voltage. For example, the instrumentation amplifier can be designed using MAX 4289Op-Amps supplied from Maxim-IC (Sunnyvale, Calif.), which can provide low power requirements of about 1.0V/90 μA and a low input offset voltage of about 200 μV.

The amplifier 138 can be a difference amplifier with low noise, which can amplify the electrical signal outputted from the Wheatstone Resistive Bridge 132 and the gain amplifier stage 136. The amplified signal from the amplifier 138 can then be transmitted to the digital signal processing device ADC in the microcontroller 140. For example, in the case where there is no gas present, the passivated and exposed sensing components such as ZnO nanorods can be similar in resistance for the Wheatstone Resistive Bridge 132, and the output sensing voltage of the gas sensor 120 through the gain amplifier stage 136 and the amplifier 138 should be approximately 0 volts.

Referring back to FIG. 1, the microcontroller 140 of the sensor device 110 can further include an ADC (i.e., A/D Converter) 142, an encoder 144, a memory 146, a decoder 148 and other components. The proper selection of these elements for the microcontroller 140 is within the discretion of one of ordinary skill.

The ADC 142 can be configured for conditioning and processing the sensing data received from the sensor interface DDI 130, particularly from the amplifier 138. In addition, the ADC 142 can be used to provide enough resolution to track the signal changes of the gas sensor 120. In various embodiments, the ADC 142 can be an onboard 10-bit ADC of the MSP 430.

The encoder 144 can be configured to encode the sensing data sampled by the ADC 142 and then store the data in the memory 146. The memory 146 assembled in the microcontroller 140 can hold software and firmware used for programming the operation of the microcontroller 140 along with other measurement circuits. The memory 146 can also retain the runtime code. The encoded data stored in the memory 146 can then be sent to the transmitter 150.

The decoder 148 can be connected to the central monitoring station 160 to process and decode the sensing data after the receiver of the central monitoring station 160 receives the signal.

The microcontroller 140 can be programmed to run as a state machine and provide two different reprogrammable modes of operation, which can include a level monitoring mode and a data transmission mode. Specifically, the level monitoring mode can be used for a detection of a gas presence, while the data transmission mode can be used for a constant tracking of gas levels. In each mode of operation; the microcontroller 140 can operate within states including, but not limited to, initialize, collect data, transmit data, and sleep.

Figure 6:
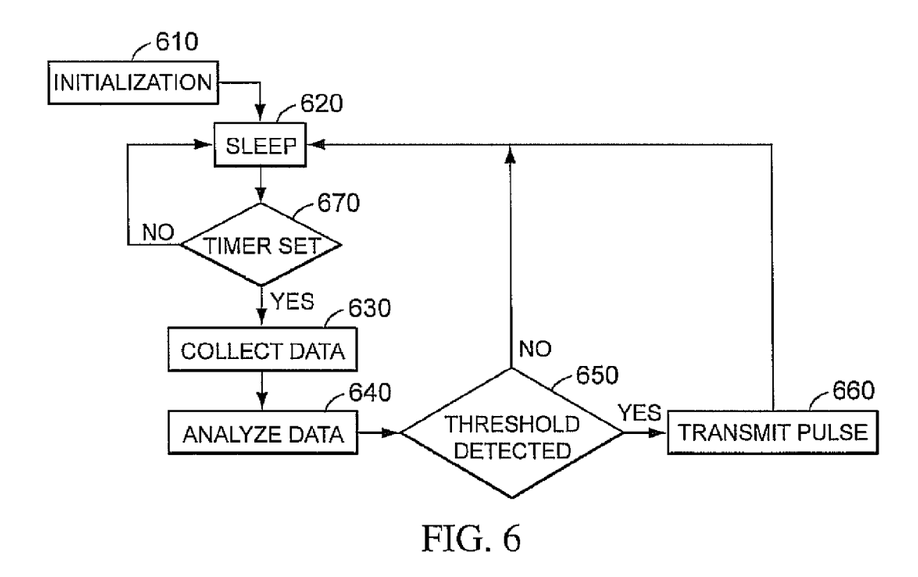
FIG. 6 is an exemplary state flow diagram for a level monitoring mode of operation of a microcontroller in accordance with the present teachings.

The level monitoring mode of operation can be used for sensing the presence of the analyte gas. FIG. 6 is an exemplary state flow diagram for the level monitoring mode of operation for the microcontroller 140. As shown, this mode can run through every state described above, for example, initialize at 610, sleep at 620, collect data at 630, and analyze data at 640, until a discernable threshold of hydrogen can be detected at 650. The discernable threshold can be a predetermined level of the gas (e.g. hydrogen) for detection. The threshold level of hydrogen can be a level of hydrogen with a concentration not to pose any serious danger. At 660, once the hydrogen can be detected, the microcontroller 140 can force the transmitter module 150 (e.g., for RF front-end) to transmit an emergency pulse to the central monitoring station 160. During the operation of this mode, a timer can be set at 670 to monitor the time for such as sample taking in FIG. 6.

Figure 7:
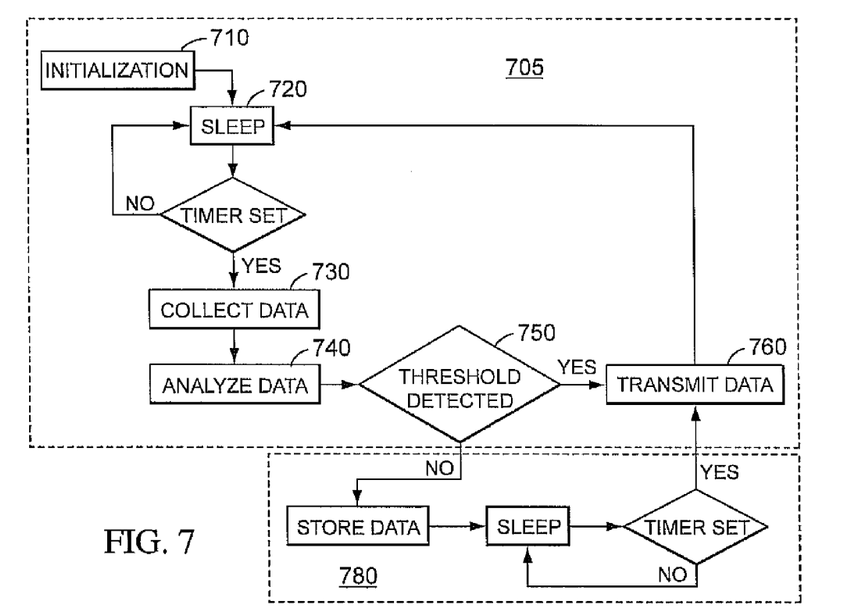
FIG. 7 is an exemplary state flow diagram for a data transmission mode of operation of a microcontroller in accordance with the present teachings.

The data transmission mode of operation of the microcontroller 140 can be used for a constant data transmission. FIG. 7 is an exemplary state flow diagram for the data transmission mode of operation including an operation process 705. As shown, the operation process 705 can be a similar process as for a level monitoring mode shown in FIG. 6 running through every state, for example, initialize at 710, sleep at 720, collect data at 730, and analyze data at 740, until a discernable threshold of hydrogen can be detected at 750. In comparison to the level monitoring mode in FIG. 6, an extra process 780 can be added for the data transmission mode in FIG. 7. The operation process 780 can queue the collected data and transmit them at 760 in FIG. 7 to the central monitoring station 160 (see FIG. 1). For example, under a constant data transmission operating mode, the sensor interface DDI 130 can detect a rising amount of the gas such as hydrogen and thus show a change in the transmitted data pattern.

The microcontroller 140 can return back to an idle mode after each operation mode. Generally, a constant data transmission mode can have a higher power requirement than the level monitoring operation mode. In various embodiments, a minimum energy coding program can be configured for the data transmission mode to further decrease the power consumption for data transmission.

Thus, the microcontroller 140 can be reprogrammable and consume a low or minimal amount of power. An exemplary microcontroller 140 can be Texas Instrument's MSP430F1232IPW (Dallas, Tex.), since it can provide pertinent features of, for example, a program memory of about 8 kB, a supply voltage ranging about 1.8 V to 3.6 V, an active mode of 200 µA at 1 MHz and 2.2 voltage supply, and a standby mode at 0.7 µA with a number of power saving modes of about 5.

Table 1 shows sensing results of an exemplary system 100 configured with an exemplary low power microcontroller for hydrogen detection using ZnO nanorods as the sensing components. Specifically, the exemplary microcontroller can include an onboard 10-bit ADC of the MSP 430 with a supply voltage of 2 volts. The ADC used can provide a resolution of about 2 mV with 1024 voltage levels between 0 and 2V.

TABLE 1

| Supply voltage | ZnO Resistance | ppm of Hydrogen | Sensor Output |
| --- | --- | --- | --- |
| 2 v | 1565 Ω | 0 | 80 uV |
| 2 v | 1521 Ω | 10 | 138 mV |
| 2 v | 1500 Ω | 500 | 240 mV |

As shown in Table 1, the resistance for the sensing components ZnO nanorods can be detected by the sensor interface DDI 130. In addition, since the ADC 142 resolution can be 2 mV, the output of the sensor interface DDI 130 can provide at least a 2 mV per ohm (i.e., output voltage per resistance change of the sensing components) output. Comparing this voltage output with the "sensor outputs" in Table 1, the exemplary system 100 can detect a hydrogen presence of about 10 ppm.

After the signal processing from the microcontroller 140, the sensor data can be sent by the transmitter module 150 configured with an antenna operating at a certain frequency, such as 916 MHz, to a remote wireless link. The antenna can be designed as a low-cost low-profile printed loop antenna. The antenna can also be fabricated on the circuit board. In various embodiments, the antenna can be located in the transmitter module 150.

The transmitter module 150 can accept the encoded data from the microcontroller 140 via a serial output port, which can also source enough power to drive and power the transmitter module 150. In various embodiments, the transmitter module 150 can connected to the energy harvesting device for a power use.

The transmitter module 150 can serve as for example a RF front end for the remote wireless link of the system 100. The transmitter module 150 can be selected with an ultra-low power consumption operation without sacrificing the transmission distance. The modulation scheme of the transmitter 150 can use a technique known as "carrier present, carrier absent", which can also be known as "On Off Keying" (OOK). An OOK transmitter can function such that the OOK transmitter can be "on" and consuming power only when the RF front end is transmitting a "high" or a "1" level. On the other hand, if the transmission is with a "low" or a "0" level, a very small amount or no power can be consumed by the OOK transmitter.

The architecture of the transmitter module 150 can be selected based on its colpitts oscillator design, which can be known to those skilled in the art and can include a single transistor and a LC tank to tune the transmitter to oscillate at a specific frequency. In various embodiments, the transmitter module 150 can be selected using a Ming TX-99 transmitter supplied from WZ Micro at San Leandro, Calif. For example, the Ming TX-99 can serve as the RF front end when it is tuned to 300 MHz. In this case, if biased at 0.6 V, the transmitter 150 can drain 850 μA, which can translate a power requirement of 510 μW to transmit a constant 50% duty cycle 580 mV peak to peak pulse train of 1 kHz. In addition, a ¼ wave 22 gauge copper monopole antenna tapped at one of the inductors of LC tank can be used to increase the transmission distance. In various embodiments, the transmitter module 150 can be assembled including the gas sensor 120.

The transmitter module 150 can further communicate to the central monitoring station 160. The central monitoring station 160 can include a receiver 162 connected to a data acquisition device 164 and a display device 166.

The receiver 162 can be a LC (where L represents an inductor and C represents a capacitor known to one of ordinary skill in the art) based receiver module tuned to a desired frequency. For example, the receiver 162 can be a Ming RE-99 receiver module tuned to 300 MHz, which can be consistent with the frequency used by the transmitter module 150. The receiver 162 can include an antenna as the radio frequency interface, which can be consistent with the antenna used for the transmitter module 150. The receiver 162 can be further connected to the decoder 148 in the microcontroller 140 to process and decode the sensor data after the receiver 152 receives the signal and down-converts the signal to a low frequency.

The data acquisition device 164 can be tied to the transmitter module 150 through the receiver 162. The data acquisition device 164 can decipher the output of the receiver 162 and display the information onscreen in a graphical user interface (GUI) written, for example, in Labview code. The data acquisition device 164 can be selected using a Labview USB-6008 data acquisition (DAQ) device from National Instruments (Austin, Tex.).

The display device 166 can be used to display results from the system 100 including, for example, the voltage reading shown the detected voltage at the remote gas sensor 120 and the change of the sensed voltage indicating the detection of hydrogen leakage. The display device 166 can be a conventional LCD, LED or other conventional display that can be driven by the data acquisition device 164 or the microcontroller 140. In various embodiments, the display device 166 can be configured with a laptop computer, where the receiver 152 and the data acquisition device 154 can be powered from the USB port of the laptop computer.

The power source 170 can be used to provide energy primed for use by one or more of the gas sensor 120, the sensor interface DDI 130, the microcontroller 140, and the transmitter module 150 in the sensor device 110. In various embodiments, the power source 170 can extract energy from various energy sources, for example, vibrational energy sources, solar energy sources, or batteries.

Figure 8:
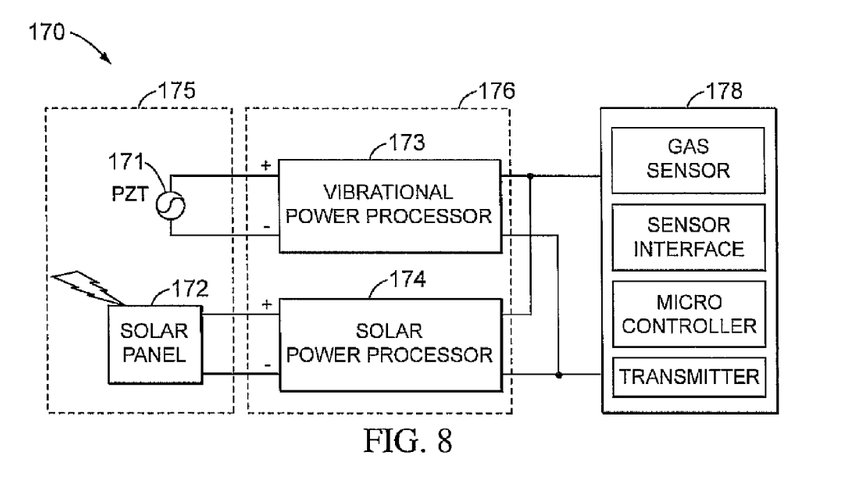
FIG. 8 depicts an exemplary power source in accordance with the present teachings.

FIG. 8 depicts an exemplary power source 170 using energy harvesting techniques to self power the sensor device 110. As shown, the power source 170 can include an energy source 175 connected to a power processor 176 and users 178. Accordingly, the energy can be harvested from the energy source 175 and processed by the power processor 176 and then provided to the users 178. The energy source 175 can include multiple energy sources, such as, for example, a PZT device 171, a solar panel 172 or other energy sources.

The power processor 176 can be configured to manage all harvested energy from the multiple energy sources in 175. In various embodiments, various power processors can be included in 176 to process their respective energy source. For example, the power processor 176 can include a vibrational power processor 173, and a solar power processor 174. In this case, the vibrational energy collected from a PZT device 171 can be connected and managed by the vibrational power processor 173. Likewise, the solar energy collected by the solar panel 172 can be connected and managed by the solar power processor 174. The harvested vibration and/or solar energy can then be consumed by the users 178.

The users 178 can be one or more component of the sensor device 110 in the system 100, including the low power gas sensor 120, the DDI 130, the microcontroller 140, and/or the transmitter module 150. In various embodiments, the users 178 can also power any other possible users onboard.

Thus, the power source 170 can include various energy harvesters, for example, the vibrational energy harvester, the solar energy harvester or other energy harvesters.

To harvest vibrational energy, the PZT device 171 can be used as an energy source with no light required. In the PZT device 171, the collection of energy (i.e., vibrational energy) can be proportional to the volume of the devices, while the limiting factors can be the magnitude and frequency of the vibrations. In various embodiments, the PZT device 171 can be selected from commercial PZT bimorph beams. In an exemplary energy harvesting device, four PSI D220-A4-203YB Double Quick Mounted Y-Pole Benders from Piezo System, Inc. (Cambridge, Mass.) can be selected for the PZT device.

The power processor 176 or the vibrational power processor 173 in 176 can be used to manage the collected vibrational power, which can include power management circuits. For example, the vibrational power processor 173 can include a direct charging circuit for power management. The direct charging circuit can include, for example, a full-bridge rectifier and a shunt capacitance, which are known to those skilled in the art. By adjusting the proof mass on the PZT device 171, the resonant frequency of the device can be changed.

In various embodiments, the vibrational energy harvester can be tested under lab conditions. For example, a mechanical shaker tuned to 1 $G_{rms}$ at 130 Hz (which can be a resonant frequency of the selected bimorph beam) can be used as a vibration source. As a result, such design can be sufficient to provide a power of 250 μW to drive the sensor device 110, i.e., the users 178.

To harvest solar energy, the solar panel 172 can include photovoltaic devices, which can offer the availability of high energy density per area. The photovoltaic devices can be an off the shelf item, such as, IXOLAR™ solar cells, for example, IXOLAR XOD 17-04B solar cell, as an input of energy to the solar power processor 174.

The power processor 176 or the solar power processor 174 in 176 can also include a power management circuits. For example, the solar power processor 174 can include a power IC device, which can be described as a Pulse Resonant Power Converter designed to be self-powered and self-controlled for maximum power point tracking and low switching loss. In addition, the Pulse Resonant Power Converter can convert an input voltage of, for example, about 0.8-1.2 volts to a steady out voltage of for example about 2 volts, which can be used to power the users 178 for the system 100.

In various embodiments, the solar power harvester can also be tested in lab conditions using a flash light as the energy source. As a result, using the flashlight as solar energy source can deliver a sufficient amount of power energy to power all users 178 of the system 100.

In some embodiments, an alarm can be configured in the system 100. In other embodiments, the alarm can be connected to the gas regulator (or valve) of gas sources (not shown). For example, a programmed threshold level can trigger the alarm and/or shut off the gas regulator or valve of the gas sources.

In various embodiments, the resulting system 100 can consume a low level of power. The power analysis can be conducted by examining the power requirements for the users 178. First, the power consumption for the gas sensor 120 can be very low and determined by the configured sensing components. For example, a gas sensor with sensing components of single ZnO nanorods can consume a power of such as less than about 30 nano-watts, as an additional example, in the range of 10-30 nano-watts.

Second, the power consumption for the microcontroller 140 can be examined. For example, the power consumption for the microcontroller 140, such as for remaining idle, for outputting data via serial power, and for scanning the ADC's input, can be as low as 2.5 µW. Generally, the most power consumed by the microcontroller 140 at any time can be in the microcontroller's initialization state, which can occur only once during an initial power up of the microcontroller 140. For example, the average power consumption for the initialization state can be 3.07 mW with a peak power of 7.3 mW, while the initialization time for the microcontroller 140 can be as short as 12.5 ms.

Third, the power consumption of the transmitter 150 attached to the serial output port of the microcontroller 140 can also be examined. The transmitter module 150 can not consume power for the transmission of a logic "0" level. When the transmission is with a "high" or "1" level, for example, with about 500 µs pulse width for the Ming TX-99 transmitter, the average power can be consumed, for example, of about 261 µW with a peak of about 522 µW. As a result, the energy harvesting techniques used for the system 100 can provide energy for both modes of operation.

In addition, the power consumption analysis can also be conducted by examining the power use of the sensor interface DDI 130. This power analysis can include the power to drive the instrumentation amplifier 136 as well as the biasing circuit for the resistive bridge of 132. For example, when no detectable gas such as hydrogen is present, the sensor surface DDI 130 can consume an exemplary power of 84 µW. When the hydrogen with exemplary concentrations of about 10 ppm and 500 ppm, the sensor interface DDI 130 can consume 88.4 µW and 88.6 µW, respectively.

In various embodiments, the duty cycle of the wireless transmission and the operation of the electronic loads from such as the sensor device 110 can vary in accordance with the power availability from the power source 170.

In various embodiments, the system 100 can be used to sense various gases including, but not limited to, hydrogen, ozone, ethylene or other hydrocarbon gases. In various embodiments, multiple gas sensors 120 can be monitored and located at various locations for the system 100. The wireless network can be realized for remote detection of these various locations of the gas sensors 120 with various multiple access techniques, such as, for example, code-division multiple access (CDMA).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for gas sensing comprising:
    a gas sensor configured to provide a response to a gas, wherein a power consumption of the gas sensor is less than about 30 nano-watts;
    a differential detection interface connected to the gas sensor to provide an electrical signal based on the response to the gas;
    a microcontroller connected to the differential detection interface and programmed to process the electrical signal; and
    a transmitter connected to the microcontroller to wirelessly transmit the processed electrical signal.

2. The system of claim 1 further comprising a central monitoring station, wherein the central monitoring station comprises a wireless receiver configured to receive the processed electrical signal from the transmitter.

3. The system of claim 1, wherein the gas comprises one or more of hydrogen, ozone, and any hydrocarbon gas.

4. The system of claim 1, wherein the sensing component of the gas sensor comprises one or more of ZnO nanorods, ZnO Schottky diodes, GaN Schottky diodes, AlGaN/GaN high electron mobility transistors (HEMT) and metal-oxide semiconductor (MOS) transistors.

5. The system of claim 4 further comprising one or more of Pt, Pd, Ni, Au, Ag, Ti, and their alloys deposited on the sensing component.

6. The system of claim 4 further, wherein the sensing component is doped with one or more of Pt, Pd, Ni, Au, Ag, Ti, and their alloys.

7. The system of claim 1, wherein the gas sensor further comprises a passivated sensing component as a reference, and wherein the passivated sensing component is isolated from exposure to the gas.

8. The system of claim 1, wherein the electrical signal from the differential detection interface comprises an amplified voltage signal.

9. The system of claim 1 wherein the microcontroller comprises a level monitoring mode and a data transmission mode.

10. The system of claim 1, wherein the microcontroller executes a minimum energy coding program stored thereon for decreasing power consumption for data transmission.

11. The system of claim 1, wherein a gas concentration is determined based on the processed electrical signal.

12. The system of claim 1, wherein the gas sensor, the differential detection interface, the microcontroller, and the transmitter are configured as a single unit.

13. The system of claim 1 further comprising a plurality of gas sensors configured to sense gas in different locations.

14. The system of claim 1 further comprising a power source that provides power to one or more of the gas sensor, the differential detection interface, the microcontroller, and the transmitter.

15. The system of claim 1, wherein a response time to the detection of the gas is about 1 to about 2 seconds.

16. A method for gas sensing comprising:
    detecting an analyte gas with a sensing component, wherein the sensing component is disposed in a low power gas sensor with a power consumption of less than about 30 nano-watts;
    outputting an electrical signal through a sensor interface to a microcontroller in response to the detected analyte gas;
    processing the electrical signal by the microcontroller; and
    wirelessly transmitting the processed electrical signal using a transmitter.

17. The method of claim 16 further comprising wirelessly receiving and displaying the processed electrical signal.

18. The method of claim 16, wherein the analyte gas comprises one or more of hydrogen, ozone, and any hydrocarbon gas.

19. The method of claim 16, wherein a detectable hydrogen gas concentration is about 10 ppm.

20. The method of claim 16, wherein processing the electrical signal by the microcontroller comprises a level monitoring mode of operation that transmits an emergency pulse for gas detection.

21. The method of claim 16, wherein processing the electrical signal by the microcontroller comprises a data transmission mode of operation that transmits constant sensing data for the analyte gas.

22. The method of claim 16, wherein a response time to the detection of analyte gas is about 1 to about 2 seconds.

23. The method of claim 16 further comprising a power source to power one or more of the low power gas sensor, the sensor interface, the microcontroller and the transmitter.

24. The method of claim 23, wherein the power source comprises at least one of a vibrational energy harvester and a solar energy harvester.

25. A system for remote hydrogen sensing comprising:
a sensor device comprising a low power hydrogen sensor configured to provide sensor data in response to detection of hydrogen, a differential detection interface connected the low power hydrogen sensor with a microcontroller to amplify and process the sensor data, and a wireless transmitter connected to the microcontroller to transmit the processed sensor data;
a central monitoring station comprising a wireless receiver configured to receive the sensor data signal from the wireless transmitter of the sensor device; and
a power source to power the sensor device, wherein the power source comprises at least one of harvested vibrational energy, harvested solar energy, and a battery.

* * * * *

UNITED STATES PATENT AND TRADEMARK OFFICE
CERTIFICATE OF CORRECTION

PATENT NO. : 8,578,757 B2
APPLICATION NO. : 12/443297
DATED : November 12, 2013
INVENTOR(S) : Fan Ren et al.

It is certified that error appears in the above-identified patent and that said Letters Patent is hereby corrected as shown below:

In the Specification

Column 1,
Line 16, "INVENTIONS" should read --INVENTION--.
Line 29, "1-2 seconds" should read --1-2 seconds.--.

Column 2,
Line 5, "connected the" should read --connected to the--.

Column 5,
Line 63, "amplifier the" should read --amplify the--.

Signed and Sealed this
Thirteenth Day of May, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,578,757 B2
APPLICATION NO. : 12/443297
DATED : November 12, 2013
INVENTOR(S) : Ren et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1233 days.

Signed and Sealed this
Twenty-second Day of September, 2015

Michelle K. Lee
*Director of the United States Patent and Trademark Office*